United States Patent [19]

Yamamoto et al.

[11] Patent Number: 5,098,999
[45] Date of Patent: Mar. 24, 1992

[54] AMINO-PROTECTED DOPA DERIVATIVE AND PRODUCTION THEREOF

[75] Inventors: Yasuo Yamamoto; Yasuo Miyadera, both of Tsukuba, Japan

[73] Assignee: Hitachi Chemical Company, Tokyo, Japan

[21] Appl. No.: 569,018

[22] Filed: Aug. 17, 1990

[30] Foreign Application Priority Data

Aug. 23, 1989 [JP] Japan .................... 1-217048
Sep. 14, 1989 [JP] Japan .................... 1-238440

[51] Int. Cl.$^5$ ............... C07C 269/00; C07C 271/00; C07D 253/00
[52] U.S. Cl. ..................... 560/29; 560/27; 560/134; 560/163; 560/170; 544/1
[58] Field of Search ............ 560/29, 134, 163, 170, 560/171, 27; 544/1

[56] References Cited

U.S. PATENT DOCUMENTS

| | | | |
|---|---|---|---|
| 3,846,476 | 11/1974 | Kaiser et al. | 260/471 C |
| 3,852,338 | 12/1974 | Kaiser et al. | 260/501.12 |
| 3,859,331 | 1/1975 | Kaiser et al. | 260/471 C |
| 4,311,706 | 1/1982 | Bodor et al. | 424/301 |

OTHER PUBLICATIONS

Carpino et al., J. Org. Chem., vol. 37, No. 22, pp. 3404-3409 (1972).
Meienhofer et al., Int. J. Peptide Protein Res., vol. 13, pp. 35-42, (1979).
R. C. de L. Milton et al., Int. J. Peptide Protein Res., vol. 30, pp. 431-432 (1987).
Schön et al., Synthesis, vol. 4, pp. 303-305 (1986).
Chang et al., Int. J. Peptide Protein Res., vol. 15, pp. 59-66 (1980).

Primary Examiner—Jose G. Dees
Assistant Examiner—Porfirio Nazario
Attorney, Agent, or Firm—Antonelli, Terry Stout & Kraus

[57] ABSTRACT

3,4-Dihydroxyphenylalanine wherein the amino group is protected with a 9-fluorenylmethyloxycarbonyl group, or a derivative thereof can be produced by reacting 3,4-dihydroxyphenylalanine with a boron compound or phosphorus compound to stabilize the hydroxyl groups, followed by introduction of a 9-fluorenylmethyloxycarbonyl group thereinto.

7 Claims, 2 Drawing Sheets

AMINO-PROTECTED DOPA DERIVATIVE AND PRODUCTION THEREOF

BACKGROUND OF THE INVENTION

This invention relates to an amino group-protected 3,4-dihydroxyphenylalanine or a derivative thereof capable of chemically synthesizing 3,4-dihydroxyphenylalanine-containing peptides, and a process for producing the same.

Adhesive proteins secreted from shells such as a mussel, a barnacle, etc., have strong adhesive strength against a low energy surface of polytetrafluoroethylene, and the like. One of constitutive amino acids rich in the adhesive proteins is 3,4-dihydroxyphenylalanine (hereinafter referred to as "dopa"), which seems to have a close relation to adhesive mechanism.

Further, it is well known that dopa is a precursor of adrenaline and noradrenalin in higher animals, and is effective as a therapeutic drug for Parkinson's disease when used as a monomer. Therefore, peptides containing dopa are expected to have applications in medicines.

Thus, a technique for chemically synthesizing dopa-containing peptides in the same manner as for synthesizing normal amino acid-containing peptides has strongly been desired in order to develop novel adhesives and medicines.

In the synthesis of peptides using amino acids as starting materials by a chemical synthesizing method, it is necessary to protect functional groups such as an amino group or carboxyl group in the main chain of an amino acid, and/or an amino group, a carboxyl group or a hydroxyl group in a side chain with various protective groups, and if necessary removing (deblocking) the protective group from an intermediate, followed by participating in the reaction.

As a method for protecting an amino group in the main chain, there have been known a method of using a benzyloxycarbonyl group, a method of using a t-butyloxycarbonyl group, a method of using a 9-fluorenylmethyloxycarbonyl (Fmoc) group, etc. Among these methods, the method of using a Fmoc group has recently been noticed, since the deblocking can be carried out under mild basic conditions and chemical synthesis of peptides by a solid phase method is possible.

Protection of an amino group of some amino acids with a Fmoc group and application to peptide synthesis was first shown by L. A. Carpino et al (J. Org. Chem., 1972, 37, 3404–3409). Then, this was applied to a solid phase by J. Meienhofer et al (Int. J. Peptide Protein Res., 1979, 13, 35–42). C. Chang et. al. studied protection of an amino group with a Fmoc group in an amino acid wherein a side chain is protected with a t-butyl group, and physical properties of thus Fmoc-protected amino acid (the side chain being protected with the t-butyl group and the amino group being protected with the Fmoc group) (Int. J. Peptide Protein Res., 1980, 15, 59–66). I. Schön et al reported that 9-fluorenylmethyl pentafluorophenyl carbonate was a useful reagent for the efficient, side reaction-free introduction of N-9-fluorenylmethyloxycarbonyl protecting group into amino acids and for the subsequent preparation of their pentafluorophenyl esters (Synthesis, 1986, 4, 303–305). R. C. Milton et al reported that 9-fluorenylmethyl succinimidyl carbonate (Fmoc-ONSu) was extremely useful in the rapid and efficient preparation of Fmoc-amino acids (Int. J. Peptide Protein Res., 1987, 30, 431–432).

Comparing the case of blocking an amino group of an amino acid having a functional group such as a hydroxyl group, an amino group, a carboxyl group at a side chain with a Fmoc group, with the case of blocking an amino acid of an amino acid having a functional group of side chain protected with a t-butyl group, a t-butyloxycarbonyl group, a benzyl group or a p-toluenesulfonyl group, etc. with a Fmoc group, when the amino acid is tyrosine, the yield is 70% in the case of the hydroxyl group at the side chain being not protected (see I. Shöen et al mentioned above), while the yield is 85% in the ease of the hydroxyl group at the side chain being protected with a dichlorobenzyl group (see R. C. Milton et al mentioned above), the yield of the latter being higher than the former.

Further, it is known that dopa having two hydroxyl groups at a side chain is unstable in neutral or alkaline, but when a borate complex is formed by reacting with boric acid or a borate in an aqueous solution, the resulting complex is remarkably stable in neutral or alkaline (Japanese patent Unexamined Publication No. 48-26745).

In the case of amino acid being dopa, it was impossible to produce dopa wherein the amino group is protected with a Fmoc group by any methods due to decomposition of dopa by an influence of basic conditions caused by sodium carbonate and sodium bicarbonate for attaching the Fmoc group. Thus, it was also impossible to easily produce peptides containing dopa in the molecule.

SUMMARY OF THE INVENTION

It is an object of the present invention to provide dopa wherein the amino group is protected with a Fmoc group, and a derivative thereof, which is capable of chemically synthesizing dopa-containing peptides. It is another object of the present invention to provide a process for producing such amino-protected dopa and a derivative thereof.

The present invention provides an amino-protected 3,4-dihydroxyphenylalanine or a derivative thereof represented by the formula:

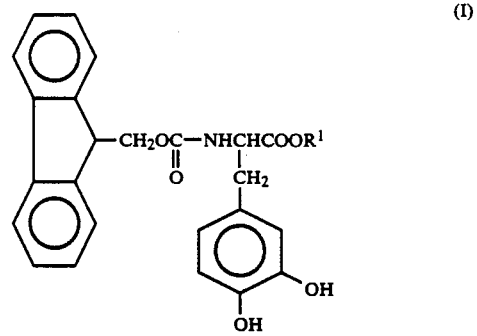

wherein $R^1$ is hydrogen, a lower alkyl group or an aryl group.

The present invention also provides a process for producing an amino-protected 3,4-dihydroxyphenylalanine or a derivative thereof represented by the formula (I), which comprises reacting 3,4-dihydroxyphenylalanine or a derivative thereof represented by the formula:

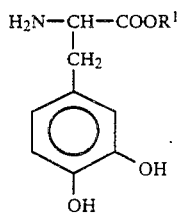

wherein $R^1$ is as defined above, with a compound capable of forming a complex with the hydroxyl groups attached to the benzene ring of the compound of the formula (II) to stabilize the hydroxy groups, and introducing a 9-fluorenylmethyloxycarbonyl (Fmoc) group thereinto.

DESCRIPTION OF THE PREFERRED EMBODIMENTS

Figure 1:
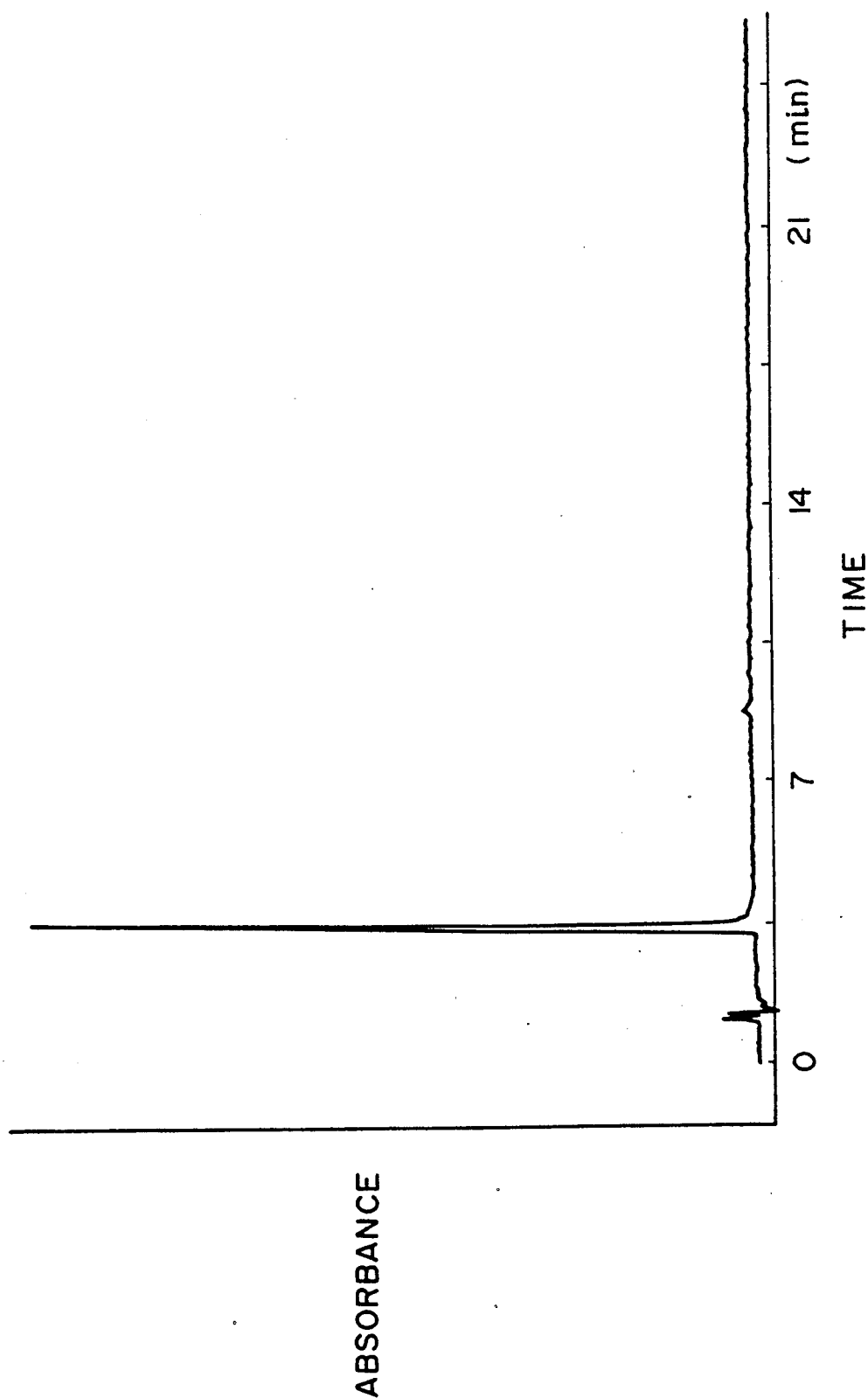
FIG. 1 is a high performance liquid chromatogram of the compound of the formula (I) wherein $R^1$ is hydrogen.

The compound of the formula:

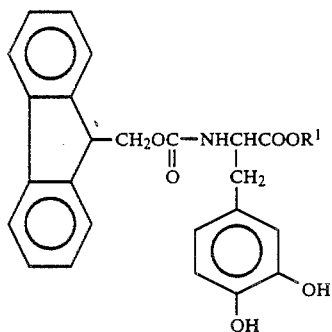

wherein $R^1$ is hydrogen, a lower alkyl group preferably having 1 to 6 carbon atoms, or an aryl group, can be used for chemically synthesizing dopa-containing peptides useful as adhesives and various medicines. The aryl group in the formula (I) includes a phenyl group, a pentachlorophenyl group, a pentafluorophenyl group, a benzyl group, a p-nitrophenyl group, or a group of the formula:

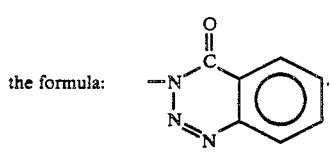

Examples of the compound of the formula (I) are as follows:

N-9-fluorenylmethoxycarbonyl-3,4-dihydroxyphenylalanine,
N-9-fluorenylmethoxycarbonyl-3,4-dihydroxyphenylalanine phenyl ester,
N-9-fluorenylmethoxycarbonyl-3,4-dihydroxyphenylalanine pentachlorophenyl ester,
N-9-fluorenylmethoxycarbonyl-3,4-dihydroxyphenylalanine pentafluorophenyl ester,
N-9-fluorenylmethoxycarbonyl-3,4-dihydroxyphenylalanine benzyl ester,
N-9-fluorenylmethoxycarbonyl-3,4-dihydroxyphenyalanine p-nitrophenyl ester,
N-9-fluorenylmethoxycarbonyl-3,4-dihydroxyphenylalanine 1-oxo-2-hydroxy-dihydrobenzotriazine ester, etc.

The compound of the formula (I) can be produced by stabilizing hydroxyl groups of a compound of the formula:

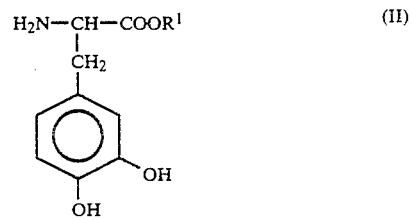

wherein $R^1$ is as defined above, with a compound capable of forming a complex with the hydroxyl groups attached to the benzene ring of the formula (II), and introducing a Fmoc group thereinto.

As the compound of the formula (II), there can be used either L-form, D-form or DL-form. The compound of the formula (I) wherein $R^1$ is hydrogen (=dopa) can easily be available commercially in reagent grade.

In the compound of the formula (II), examples of the lower alkyl group of $R^1$ are a methyl group, an ethyl group, a n-propyl group, an isopropyl group, an n-butyl group a t-butyl group, etc. Introduction of these groups can be carried out by reacting with a corresponding anhydrous alkyl alcohol under acidic conditions.

Examples of the aryl group ($R^1$) in the formula (II) are a phenyl group, a pentachlorophenyl group, a pentafluorophenyl group, a benzyl group, a p-nitrophenyl group, a group of the formula:

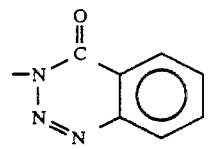

When $R^1$ is a pentachlorophenyl group, a pentafluorophenyl group, a p-nitrophenyl group or a group of the formula:

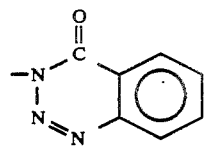

the amino group and the hydroxyl groups of dopa are previously protected with a suitable protective group conventionally used, followed by reaction with a corresponding phenol derivative and deblocking of the protective group from the amino group and the hydroxyl group to introduce such a group as $R^1$.

As the compound capable of forming a complex with the hydroxyl groups attached to the benzene ring of the formula (II), there can be used boron compounds and phosphorus compounds.

Examples of the boron compounds are sodium tetraborate, sodium m-borate, potassium tetraborate, potassium m-borate, etc.

Examples of the phosphorus compounds are trisodium phosphate, disodium phosphate, sodium phosphate, tripotassium phosphate, dipotassium phosphate, potassium phosphate, etc.

In the present invention, at least one compound of these compounds is used. The amount of the boron compound or phosphorus compound is a sufficient amount of boron or phosphorus to form a complex with a compound of the formula (II).

The reaction of a boron compound or a phosphorus compound with a compound of the formula (II) is carried out with stirring under conditions, e.g. pH, temperature and reaction time, suitable for forming the above-mentioned complex. Preferable pH is 7 to 12 more preferably pH 7.2 to 10, preferable temperature is 0° to 100° C. and preferable reaction time is 3 minutes to 24 hours. Thus, the hydroxyl groups on the benzene ring of the compound of the formula (II) can be stabilized.

After stabilizing, the resulting complex is reacted with an agent for introducing a Fmoc group. As the agent for introducing a Fmoc group, there can be used 9-fluorenylmethyl chloroformate (Fmoc-Cl), 9-fluorenylmethyl pentafluorophenyl carbonate, 9-fluorenylmethyl N-succinimidyl carbonate, etc.

The introduction of the Fmoc group can preferably be carried out, for example, at a pH of 7 to 12, more preferably 8 to 12, and a temperature of 0° to 100° C. for 1 minute to 6 hours with stirring. As an agent for adjusting the pH, there can preferably be used sodium carbonate, sodium bicarbonate, etc.

The reaction of the compound of the formula (II) with the compound capable of forming a complex with the hydroxyl groups attached to the benzene ring of the formula (II), and the reaction of introducing the Fmoc group can be carried out in a solvent. As the solvent, there can be used water, and an organic solvent such as acetonitrile, diethyl ether, dioxane, acetone, etc., or a mixture thereof.

These reactions can be carried out under an atmosphere. In order to suppress side reactions as low as possible, it is preferable to carry out these reactions under an inert gas such as argon, etc.

The thus produced compound is taken out of the reaction solution which is made acidic (e.g. pH 1-6) with an acid such as hydrochloric acid, sulfuric acid, or the like, by extraction with an organic solvent such as ether, ethyl acetate, tetrahydrofuran, dichloromethane, chloroform, etc. After removing the organic solvent by a suitable method, e.g. condensation under reduced pressure, the resulting product is recrystallized from a mixed solvent such as dichloromethane/hexane, methanol/ethanol, etc., and, if necessary, subjected to a purification procedure such as column chromatography to give a purified product of the formula (I).

When the resulting compound of the formula (I) has a group other than a hydrogen atom, it can be provided for chemical synthesis of dopa-containing peptides after protecting the carboxyl group with a pentafluorophenyl group, or the like, and further, if necessary, protecting the hydroxyl groups on the benzene ring with a t-butyl group, or the like.

When the resulting compound of the formula (I) has a hydrogen atom, it can be provided for chemical synthesis of dopa-containing peptides after protecting the hydroxyl groups on the benzene ring with a t-butyl group, or the like, or protecting the hydroxyl groups on the benzene ring with a t-butyl group, or the like and at the same time, protecting the carboxyl group with a pentafluorophenyl group, or the like.

The present invention is illustrated by way of the following Examples.

EXAMPLE 1

To 593 mg (3 mmoles) of 3,4-dihydroxyphenyl-L-alanine (mfd. by Sigma Chemical Co.), a mixed solvent of 20 ml of acetonitrile and 10 ml of acetone was added, and further 30 ml of 0.01M sodium tetraborate buffer solution (pH 9.18) was added, followed by stirring at room temperature for 15 minutes. To the resulting mixture, 1015 mg (3 mmoles) of 9-fluorenylmethyl N-succinimidyl carbonate (mfd. by Cambridge Research Biochemicals Co., Ltd.) was added and stirred at room temperature for 12 hours. To the mixed reaction solution, 788 mg (7.4 mmoles) of sodium carbonate was added little by little, and stirred for further 5 minutes. Unreacted starting materials were extracted with 15 ml of ether thrice, and concentrated hydrochloric acid was added to an aqueous layer to make the pH 2. From the aqueous layer, the reaction product was extracted with 20 ml of ethyl acetate thrice, and the ethyl acetate layer was washed with 20 ml of 0.1N aqueous solution of hydrochloric acid once. The ethyl acetate solution was dried by anhydrous magnesium sulfate, and the ethyl acetate was removed by distillation. The residue was recrystallized from dichloromethane/hexane to give 271 mg of the reaction product in yield of 67%.

Analyfical results of the reaction product were as follows.

Figure 2:
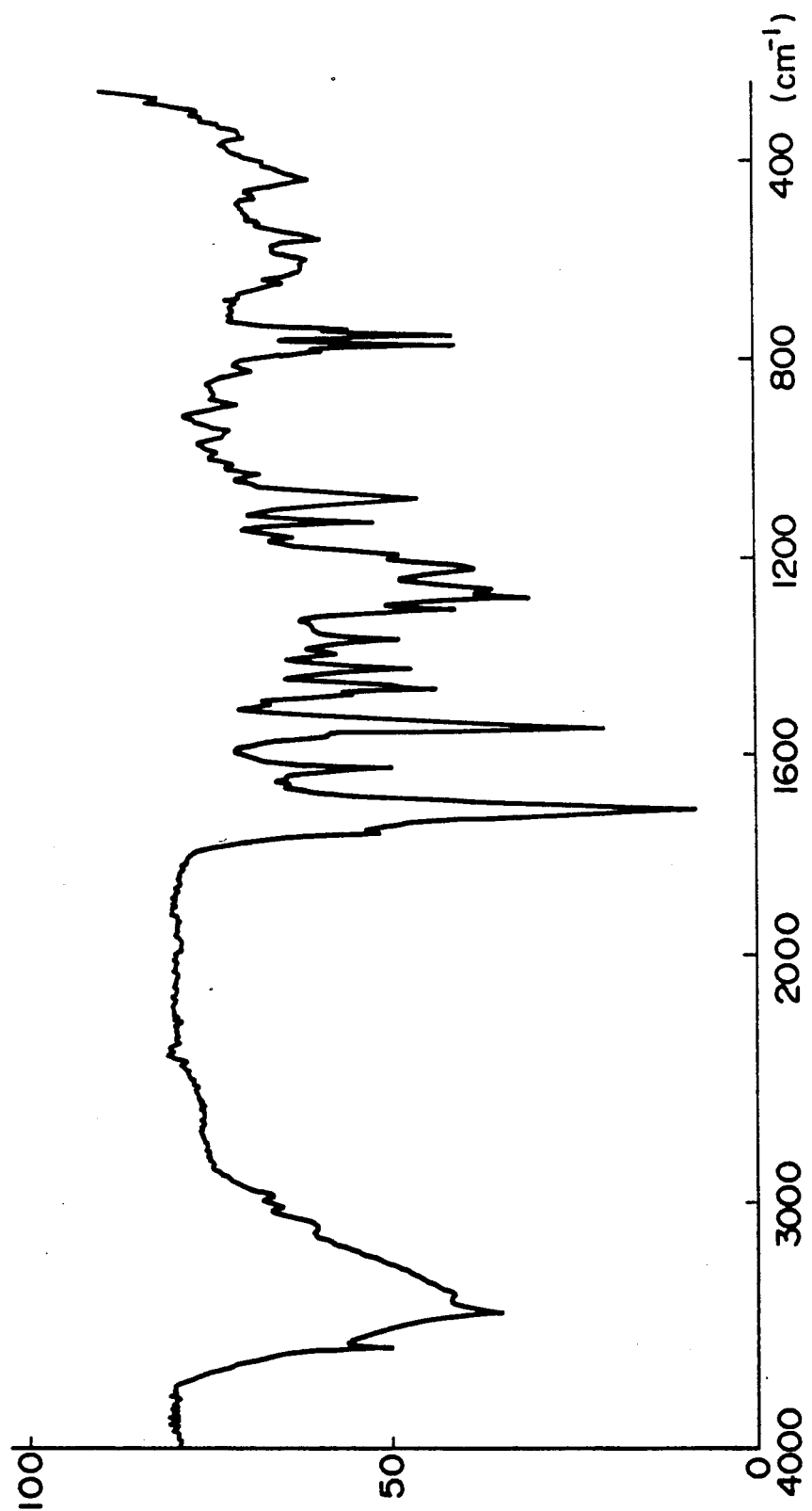
FIG. 2 is an infrared spectrum of the compound of the formula (I) wherein $R^1$ is hydrogen.

Melting point: 159° C.
$^1$H NMR spectrum: Table 1.
$^{13}$C NMR spectrum: Table 2.
High performance liquid chromatogram: FIG. 1.
Infrared absorption spectrum: FIG. 2.

In FIG. 1, the reaction product is expressed at the holding time of 3–4 minutes. Under the same analytical conditions, a starting material of 3,4-dihydroxyphenyl-L-alanine appears at the holding time of 1–2 minutes, and another starting material of 9-fluorenylmethyl N-succinimidyl carbonate appears at the holding time of 8–9 minutes.

From the above-mentioned results, the resulting reaction product was confirmed to be a compound of the formula:

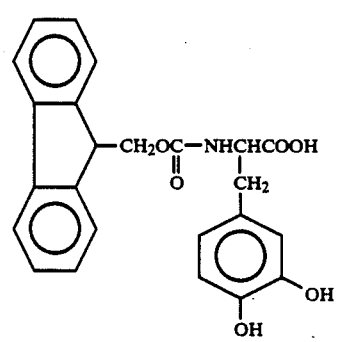

(III)

The melting point was measured by using a differential thermal scanning calorimeter (DSC-7 type, mfd. by Perkin-Elmer Corp.) at a temperature rise rate of 10° C./min with a sample amount of 1.8 mg.

$^1$H NMR and $^{13}$C NMR spectra were measured by using a nuclear magnetic resonance apparatus (AC-250 type, mfd. by Bruker Co., Ltd.).

High performance liquid chromatography (measuring apparatus: 600 Series, mfd. by Waters, Division of MILLIPORE) was carried out using as a column μ Bondasphere 5μ C18-100 Å (3.9 mm ×15 cm, mfd. by Waters), as an eluent a 50:50 mixed solution of 0.1% trifluoroacetic acid-water and 0.1% trifluoroacetic acid-acetonitrile, with a flowing amount of 1.0 ml/min and detecting wavelength of 220 nm.

Infrared absorption spectrum was measured by using an infrared analysis apparatus (270-50 type, mfd. by Hitachi, Ltd.) and a KBr tablet method.

TABLE 1

| $^1$H NMR spectrum (250 MHz, acetone - d$_6$, δ value, ppm) |
| --- |
| 7.84 (dd, 2H), 7.66 (brd. d, 2H), 7.39 (ddd, 2H), 7.31 (ddd, 2H), 6.82 (d, 1H), 6.76 (d, 1H), 6.64 (dd, 1H), 6.64 (brd, 1H), 4.46 (m, 1H), 4.33~4.17 (m, 3H), 3.11 (dd, 1H), 2.91 (dd, 1H) |

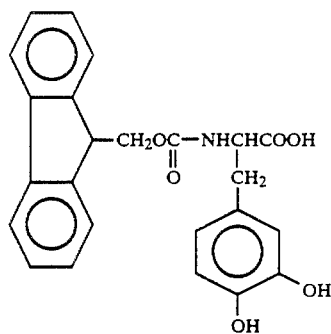

(III)

TABLE 2

| $^{13}$C NMR spectrum (62.89 MHz, acetone - d$_6$, δ value, ppm) |
| --- |
| 173.4, 156.7, 145.8, 145.0, 144.7, 142.0, 129.8, 128.4, 127.9, 120.7, 126.2, 121.5, 117.1, 116.0, 67.2, 56.4, 47.9, 37.6. |

EXAMPLE 2

To 591 mg (3 mmoles) of 3,4-dihydroxyphenyl-L-alanine and 1145 mg (3 mmoles) of sodium tetraborate. 10 hydrate, 40 ml of water was added and stirred at room temperature for about 60 minutes. Then, 10 ml of acetonitrile dissolving 1018 mg (3 mmoles) of 9-fluorenylmethyl N-succinimidyl carbonate was added to the resulting mixture and stirred at room temperature for 17 hours. To the mixed reaction solution, 5.0 g of sodium carbonate was added little by little and stirred at room temperature for about 10 minutes. Unreacted starting materials were extracted with 20 ml of ether thrice, and an aqueous layer was made pH 2 with concentrated hydrochloric acid. From the aqueous layer, the reaction product was extracted with 20 ml of ether thrice. The extract was dried by anhydrous magnesium sulfate, and the ther was removed by distillation. The residue was recrystallized from methanol/ethanol to give 1100 mg of the reaction production in yield of 87%.

The analytical results of the reaction product revealed that the melting point, $^1$H NMR spectrum, $^{13}$C NMR spectrum, high performance chromatogram and infrared absorption spectrum were the same as those obtained in Example 1 to confirm that the reaction product was the compound of the formula (III).

EXAMPLE 3

To 591 mg (3 mmoles) of 3,4-dihydroxyphenyl-L-alanine and 524 mg (3 mmoles) of potassium monohydrogen phosphate, 40 ml of water was added and stirred at room temperature for about 60 minutes. Then, 10 ml of acetonitrile dissolving 1017 mg (3 mmoles) of 9-fluorenylmethyl N-succinimidyl carbonate was added to the resulting mixture and stirred at room temperature for 17 hours. To the resulting mixed reaction solution, 5.0 g of sodium carbonate was added little by little, and stirred at room temperature for about 10 minutes. Unreacted starting materials were extracted with 20 ml of ether thrice, and an aqueous layer was made pH 2 with concentrated hydrochloric acid. From the aqueous layer, the reaction product was extracted with 20 ml of ether thrice. The extract was dried by anhydrous magnesium sulfate. After removing the ether by distillation, the residue was recrystallized from methanol/ether to give 867 mg of the reaction product in yield of 68%.

The analytical results of the reaction product revealed that the melting point, $^1$H NMR spectrum, $^{13}$C NMR spectrum, high performance chromatogram and infrared absorption spectrum were the same as those obtained in Example 1 to confirm that the reaction product was the compound of the formula (III).

As mentioned above, according to the present invention, dopa wherein the amino group is protected by a Fmoc group, and a derivative thereof can be produced easily. Using the amino-protected dopa and a derivative thereof, it becomes possible to chemically synthesize dopa-containing peptides.

What is claimed is:

1. An amino-protected 3,4-dihydroxyphenylalanine or a derivative thereof represented by the formula:

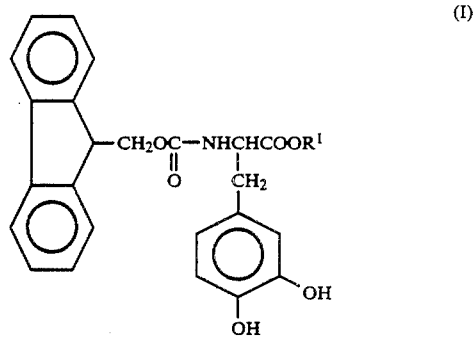

(I)

wherein R$^1$ is hydrogen, a lower alkyl group, an aryl group or a group of the formula:

the formula: 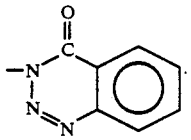

2. An amino-protected 3,4-dihydroxyphenylalanine or a derivative thereof according to claim 1, which is

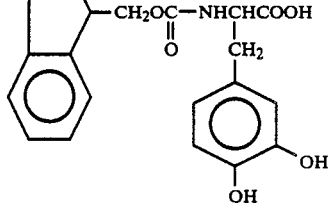

3. An amino-protected 3,4-dihydroxyphenylalanine or a derivative thereof according to claim 1, wherein the aryl group represented by $R^1$ in the formula (I) is a phenyl group, a pentachlorophenyl group, a pentafluorophenyl group, a benzyl group, or a p-nitrophenyl group.

4. An amino-protected 3,4-dihydroxyphenylalanine or a derivative thereof according to claim 1, wherein $R^1$ in the formula (I) is a lower alkyl group.

5. An amino-protected 3,4-dihydroxyphenylalanine or a derivative thereof according to claim 1, wherein $R^1$ in the formula (I) is a group of the formula:

the formula: 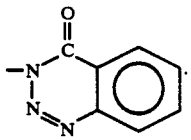

6. A process for producing an amino-protected 3,4-dihydroxyphenylalanine or a derivatie thereof represented by the formula:

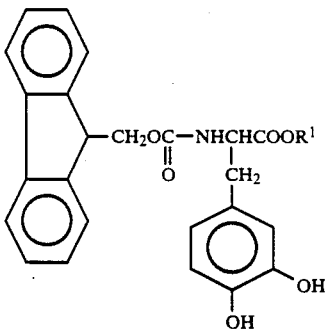 (I)

wherein $R^1$ is hydrogen, a lower alkyl group an aryl group, or a group of the formula:

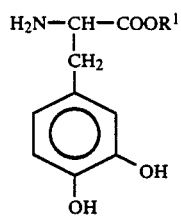

which comprises reacting 3,4-dihydroxyphenylalanine or a derivative thereof represented by the formula:

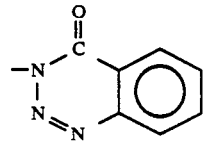 (II)

wherein $R^1$ is as defined above, with a boron compound selected from the group consisting of sodium tetraborate, sodium m-borate, potassium tetraborate, and potassium m-borate, or a phosphorus compound selected from the group consisting of trisodium phosphate, disodium phosphate, sodium phosphate, tripotassium phosphate, dipotassium phosphate and potassium phosphate at pH 7 to 12 to form a complex wherein the hydroxyl groups of the compound of the formula (II) are stabilized, reacting the complex with 9-fluorenylmethyl chloroformate, 9-fluorenylmethyl pentafluorophenyl carbonate, or 9-fluorenylmethyl N-succinmidyl carbonate at pH 7 to 12, and making the resulting reaction solution acidic.

7. A process according to claim 6, wherein the reaction for forming the complex is carried out at 0° to 100° C. and the reaction with the complex is carried out at 0° to 100° C.

* * * * *